United States Patent [19]

Suzuki et al.

[11] Patent Number: 4,990,795
[45] Date of Patent: Feb. 5, 1991

[54] PARTICLE COUNTER WITH PHOTOINTENSITY COMPENSATION

[75] Inventors: Riichiro Suzuki; Yoshihiro Kubo, both of Miyanohigashi, Japan

[73] Assignee: Horiba, Ltd., Kyoto, Japan

[21] Appl. No.: 382,548

[22] Filed: Jul. 19, 1989

[30] Foreign Application Priority Data

Jul. 30, 1988 [JP] Japan ................ 63-191282

[51] Int. Cl.$^5$ ................ G01N 15/06; G01N 21/49; G01N 21/85
[52] U.S. Cl. ................ 250/574; 356/339
[58] Field of Search ........... 250/574; 356/337, 338, 356/339, 441, 442; 340/627

[56] References Cited

U.S. PATENT DOCUMENTS

| | | | |
|---|---|---|---|
| 3,703,641 | 11/1972 | Rosen | 356/336 |
| 3,786,261 | 1/1974 | Tucker | 250/574 |
| 3,901,602 | 8/1975 | Gravatt, Jr. | 250/574 |
| 4,242,194 | 12/1980 | Steiner et al. | 356/337 |
| 4,247,783 | 1/1981 | Berber et al. | 250/574 |
| 4,265,538 | 5/1981 | Wertheimer | 356/336 |
| 4,318,180 | 3/1982 | Lundqvist et al. | 356/336 |
| 4,676,641 | 6/1987 | Bott | 356/338 |
| 4,781,459 | 11/1988 | Suzuki | 356/339 |
| 4,783,599 | 11/1988 | Borden | 250/574 |
| 4,830,494 | 5/1989 | Ishikawa et al. | 250/574 |

Primary Examiner—David C. Nelms
Assistant Examiner—Stephone B. Allen
Attorney, Agent, or Firm—Price, Gess & Ubell

[57] ABSTRACT

A particle counter for measuring the concentration and particle-size distribution of minute particles in a fluid by irradiating the particles with a laser beam from a direction that is substantially perpendicular to the fluid flow direction and by detecting the light scattered from the particles. The laser beam, prior to irradiating the particles, is flattened with a lens system and its otherwise Gaussian photointensity distribution is converted to a square pattern with a slit member. The light scattered from a central portion of the fluid is detected and formed into a real image with a focusing lens system and a detecting slit that cuts the real image only in the irradiating direction. The scattered light may be detected from a third direction that is substantially perpendicular to the flow direction and the irradiating direction.

6 Claims, 4 Drawing Sheets

PARTICLE COUNTER WITH PHOTOINTENSITY COMPENSATION

BACKGROUND OF THE INVENTION

1. Field of the Invention

The present invention relates to a particle counter for measuring the concentration (quantity) and the particle-size distribution of minute particles (organic substances, dust, bacteria and the like) contained in a fluid. For example, the present invention may be used to control a fluid such as ultrapure water used in a process for washing wafers in the production of semiconductors and clean air in a clean room.

In particular, the present invention relates to a particle counter for counting minute particles in a fluid that is flowing at an appointed flow velocity and that has a substantially uniform flow velocity distribution comprising an irradiating optical system for irradiating a central portion of said fluid with a laser beam from the side and perpendicular to the flow direction of the fluid, and further comprising a detecting optical system for detecting light from the laser beam that is scattered by the minute particles contained in said fluid.

2. Description of Related Art

One example of a prior art particle counter is roughly shown in FIG. 4. A fluid S to be measured is flown through a flow cell (not shown) at an appointed velocity of flow by means of a nozzle 1. An irradiating optical system (a) is provided for irradiating with a laser beam a central portion, where the flow velocity distribution is uniform as far as possible, in the fluid S to be measured, from a side in a direction y (hereinafter referred to as the second direction) meeting at right angles with a flow direction z of the fluid S to be measured (hereinafter referred to as the first direction). A detecting optical system (b) is provided for detecting, from a side in said first direction z, light L' scattered by minute particles contained in said fluid S so as to measure the concentration and the particle-size distribution of the minute particles contained in said fluid S.

The irradiating optical system (a) typically includes a cylindrical lens 2 for turning said laser beam L into a flat beam (short in said first direction z and long in a direction x, hereinafter referred to as the third direction, meeting at right angles with said first direction z and said second direction y). The detecting optical system (b) is provided with a photoreceiving lens 3 and a slit member 5' having a slit 4' for delimiting a detecting range (r) by limiting an incidence of said scattered light L' in said second direction y and said third direction x at an image-forming position (position forming a real image) thereof.

However, in order to ensure the desired resolution power (in particular the particle-size resolution power) with a particle counter of the above-described conventional construction, it is necessary to conduct the measurement using only that portion of the laser beam L where the intensity of the irradiated laser beam L is almost uniform as far as possible (the vicinity of the peak at the center of the Gaussian distribution in the third direction x corresponding to the hatched portion schematically shown in FIG. 5).

In order to sufficiently delimit the source of the scattered light L', the slit member 5' of the conventional detecting optical system (b) must be provided with a remarkably narrow slit 4' which limits the detection range (r) not only in the irradiating direction of the laser beam L (second direction y), but also in the radial direction of the laser beam L (third direction x, refer to FIG. 6). Moreover, the scattered light L' must be detected from a side that is in the flow direction (first direction) z of the fluid S. Accordingly, the following disadvantages are present in the above-described prior art device:

(A) Since the detection range (r) is delimited by limiting the incident scattered light L' by means of the slit member 5' as shown in FIG. 6, a reduction in resolution power is inherent, since an outer edge portion of an image I required for the aberration of the detecting optical system (b) is cut in all circumferential portions of the slit 4'. Thus, the resolution power is fundamentally inferior and, accordingly, the aberration must be remarkably reduced by, for example, providing the detecting optical system (b) with a specialized and expensive aberration-compensating means;

(B) The slightest change in the refractive index of the fluid S leads to the dislocation of a focus in the slit member 5', whereby the undesirable phenomenon of cutting the outer edge portion of the image I by the circumferential or perimeter portions of the slit 4' is further aggravated. Thus, the slit member 5' must be repeatedly moved in order to regulate the focus, and the resolution power is still further reduced. For example, a specialized microfocus regulating means capable of precisely moving the slit member 5' dependent upon the change of the refractive index of the fluid S must be provided. This results in an expensive complication in the construction of the detecting optical system (b);

(C) As described in Paragraph (A) above, the aberration of the detecting optical system (b) must be reduced in order to ensure the resolution power. However, it is difficult to increase an openness, and the quantity of the scattered light L' received so as to improve the S/N ratio is deteriorated, while simultaneously accounting for aberration of the detecting optical system (b); and (D) Because the detecting optical system (b) must be provided on the side in the flow direction (first direction) z of the fluid S to be measured, although not shown in FIG. 4, the construction is complicated and overly large in that the fluid passage on the downstream side of the measuring portion must be bent, or a whirling flow must be used. Moreover, the control of flow velocity is apt to become difficult.

SUMMARY OF THE INVENTION

The present invention has been achieved in view of the above-described problems. It is an object of the present invention to provide a particle counter which, as a whole, is simple in construction, small in size, and inexpensive, yet capable of improving both the resolution power and the signal-to-noise ratio so that the detection range may be expanded as far as possible, so that the detecting optical system may be less apt to be influenced by the aberration and the dislocation of focus, and so that the detecting optical system may be disposed at an optional position other than the side in the flow direction of the fluid to be measured.

In order to achieve the above-described object, the particle counter according to the present invention is characterized by an irradiating optical system that is provided with a photointensity-compensating means for turning a distribution of integrated photointensity values perpendicular to the flow direction of the fluid to be measured and for turning the irradiating direction of the laser beam (value integrated in the flow direction of the fluid to be measured) into a square one. Finally, the detecting optical system is provided with a slit member that is provided with a slit having a width so that there is sufficient room in the direction meeting at a right angle with the irradiating direction of said laser beam at the image-forming position thereof.

In the particle counter according to the above-described present invention, as will be made clear from the below description of the preferred embodiments, the distribution of the integrated photointensity value of the laser beam (value integrated in the flow direction of the fluid to be measured) is turned into a square. In effect, before irradiating the central portion in the fluid where the flow velocity distribution is substantially uniform, the photointensity is compensated so as to be almost uniform as a whole in the directions that are perpendicular to the flow direction of the fluid and the irradiating direction of the laser beam by providing the irradiating optical system with the above-described photointensity-compensating means. Under the present invention, because the detection range can be delimited without limitation in the radial direction of the laser beam, it is not necessary to use only that part of the laser beam (the central portion where the intensity is almost uniform) as the detection range. Furthermore, the slit member to be provided at the image-forming position in the detecting optical system may have a slit of greater width in the direction meeting at right angles with the irradiating direction of the laser beam. In short, an increased limiting width for the detection range in the irradiating direction of the laser beam is possible without limiting the detection range in the radial direction of the laser beam.

Thus, the influences by said aberration and dislocation of focus can be remarkably suppressed in comparison to the conventional particle counter, because the phenomena of cutting the outer edge portion of the image with the detection slit due to the aberration of the detecting optical system and the dislocation of focus, caused by changes in the refractive index of the fluid, still appear on the circumferential portion of the slit in the direction perpendicular to the irradiating direction of the laser beams, but do not appear on the circumferential portion of the slit in the irradiating direction of the laser beam. Even if the detecting optical system exhibits some aberration or the focus of the slit member is dislocated to some extent due to the change in the refractive index of the fluid, the resolution power can be remarkably improved in comparison to the conventional particle counter.

A detecting optical system, in accordance with the present invention, can be made simple and inexpensive by eliminating the requirement for the special aberration-compensating means and microfocus regulating mechanism. In addition, with the particle counter according to the present invention, it is not always required to provide the detecting optical system on the side in the flow direction of the fluid to be measured. Since the particle counter can be provided at optional positions on the side and perpendicular to the flow direction of the fluid, it is not required to bend the passage downstream of the flow cell or the measuring portion, as in the conventional particle counter, allowing the particle counter to be further simplified and smaller as a whole.

DETAILED DESCRIPTION OF THE PREFERRED EMBODIMENTS

One preferred embodiment of the particle counter according to the present invention will be described below with reference to the drawings.

Figure 1:
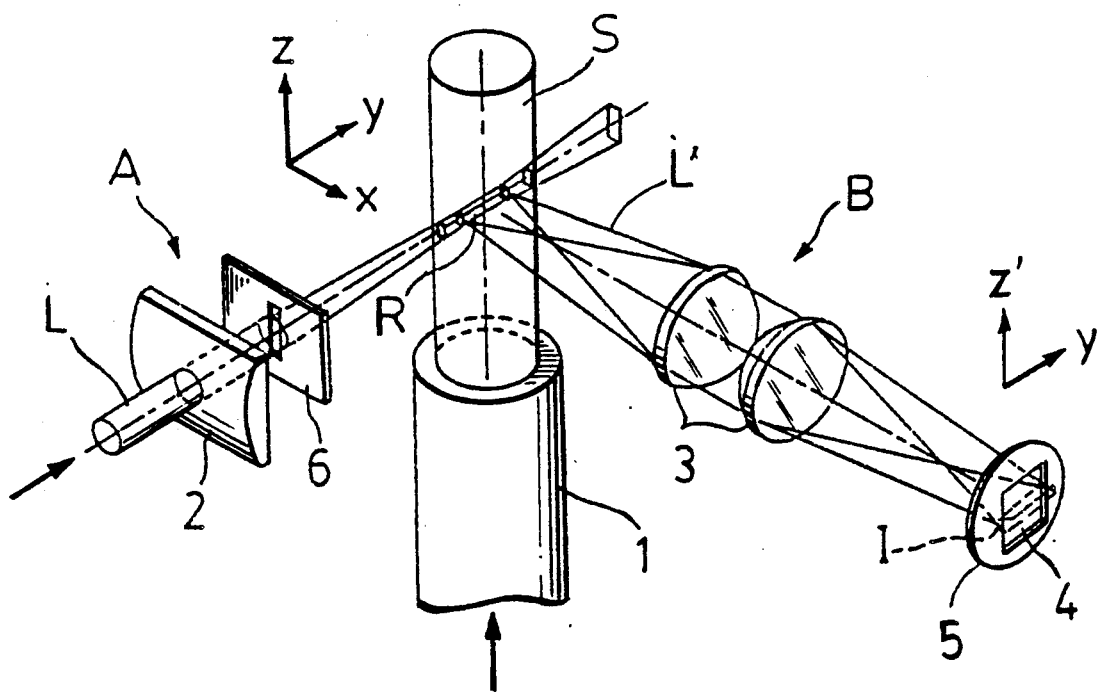
FIG. 1 is a perspective view showing principal parts of a preferred embodiment of a particle counter according to the present invention.

As shown in FIG. 1, the fluid S to be measured flows into a flow cell (not shown) at the appointed velocity of flow by means of, for example, nozzle 1. The central portion in the fluid S, where the flow velocity distribution is substantially uniform, is selected as the detection range R. An irradiating optical system (A) is provided for irradiating the detection range R with the laser beam L (for example, a helium-neon laser, an argon laser, or a helium-cadmium laser) from the side in a direction y (hereinafter referred to as the second direction) that is substantially perpendicular to the flow direction z (hereinafter referred to as the first direction) of the fluid S. A detecting optical system B is also provided for measuring the concentration and the particle-size distribution of the minute particles contained in the fluid S by detecting the scattered light L' scattered by the minute particles contained in the fluid S when the minute particles are irradiated by the laser beam L. The detecting optical system B detects the scattered light L' from the side in the direction x (hereinafter referred to as the third direction) meeting at substantially a right angle with said first direction z and said second direction y.

Figure 2:
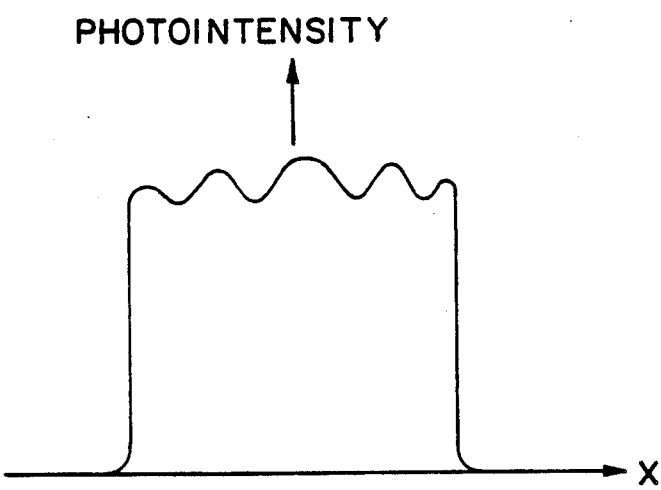
FIG. 2 is a diagram showing the intensity distribution characteristics of the laser beams irradiated to the detection range.

As further shown in FIG. 1, the irradiating optical system (A) includes a cylindrical lens 2 for turning the laser beam L into a flat beam (short in the first direction z and long in the third direction x), and a photointensity-compensating means 6 provided between the cylindrical lens 2 and said detection range R for turning the distribution of integrated photointensity values in said third direction x (values integrated in the first direction z) into a square-shaped one as shown in FIG. 2 (for example, by cutting off both end portions of the Gaussian distribution by means of a slit or by turning the distribution of integrated photointensity values into a square shape as a whole by using a beam-shape regulating means such as a space filter and a soft aperture).

Figure 3:
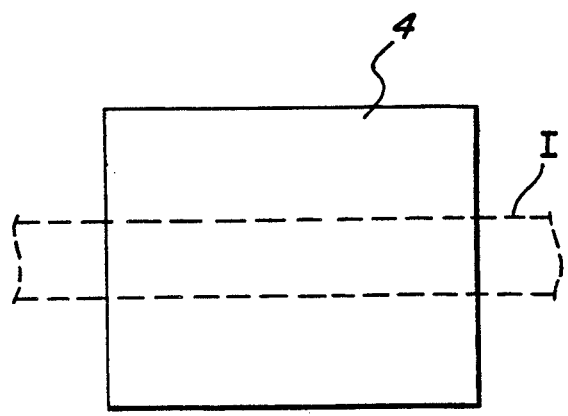
FIG. 3 is an enlarged front view showing the slit portion in the detecting optical system.
Figure 4:
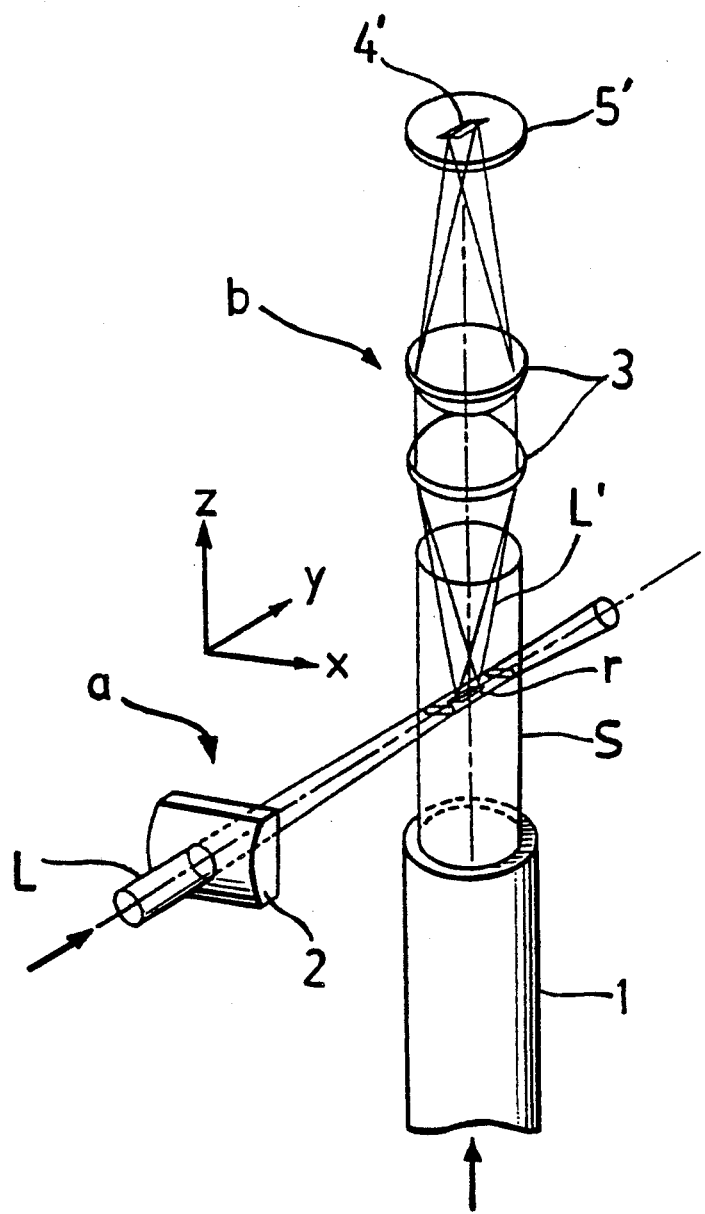
FIG. 4 is a rough block diagram (perspective view) showing principal parts of the conventional prior art particle counter.
Figure 5:
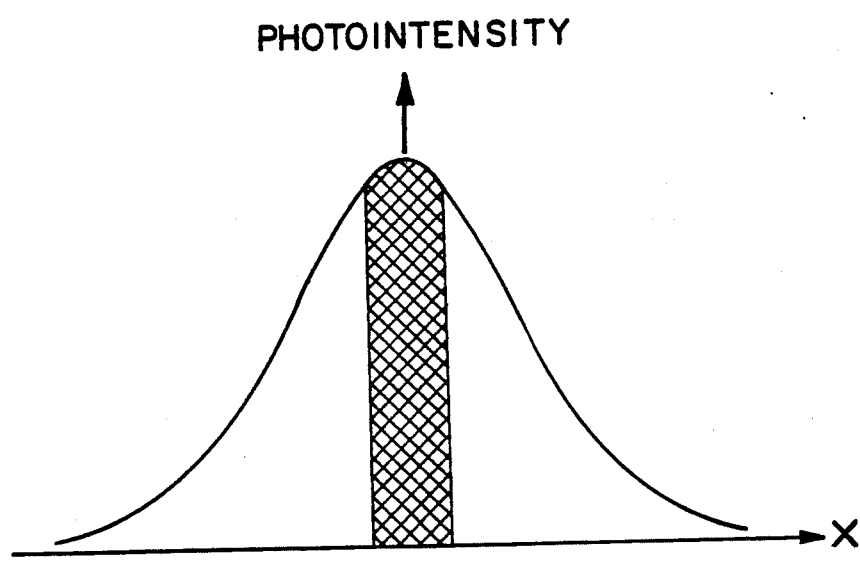
FIG. 5 is a characteristic diagram showing the distribution of integrated photointensity values of the laser beams irradiated to the detection range (values integrated in the flow direction of the fluid to be measured.
Figure 6:
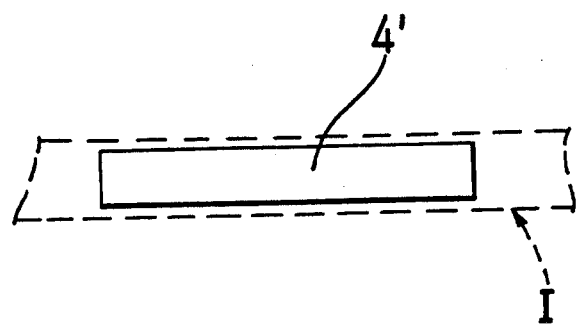
FIG. 6 is an enlarged front view showing the slit member in the detecting optical system of the prior art device shown in FIG. 4.

The detecting optical system (B) includes a photoreceiving lenses 3 and a slit member 5 that is provided with a slit 4 of sufficient width in the direction z' meeting at substantially a right angle with said second direction y. In short, the influences of aberration and dislocation of focus in the detecting optical system (B) may be remarkably suppressed in comparison to a conventional particle counter by limiting, at the image-forming position (the position where the real image is formed as shown in FIG. 3), the detection range R in the irradiating direction (second direction y) of the laser beam L, but not limiting the detection range R in the radial direction of the laser beam L, so as to only limit the incidence of said scattered light L in the second direction y and prevent the phenomenon of cutting the image I formed in the slit member 5 from being brought about in the circumferential portion of the slit 4 in the irradiating direction (second direction y) of the laser beam L.

Moreover, in the particle counter according to the above-described preferred embodiment of the present invention, the detecting optical system B need not be provided on the side in the first direction z (as in the conventional particle counter), but rather may be provided on the side in the third direction x. Hence, it is not necessary to bend the passage at the downstream side of the flow cell or the measuring portion, as in the conventional particle counter, and a large flow cell is not required as in the case where a whirling stream is used.

As obvious from the above detailed description, the particle counter according to the present invention is characterized by an irradiating optical system that is provided with the photointensity-compensating means for turning the distribution of integrated photointensity values into a square shape (values integrated in the flow direction of the fluid) in the direction substantially perpendicular to the flow direction of the fluid and the irradiating direction of the laser beam, and by a detecting optical system that is provided with the slit member with a slit of sufficient width in the direction substantially perpendicular to the irradiating direction of the laser beam at the image-forming position thereof, whereby the detrimental influences of aberration and dislocation of focus can be reduced in comparison with the conventional particle counter. Furthermore, a notably superior effect is exhibited in that the detecting optical system can be provided at optional positions other than the side in the flowing direction of the fluid to be measured, whereby the particle counter can be made simple and smaller as a whole.

What is claimed is:

1. A particle counter for measuring the concentration and particle-size distribution of minute particles contained in a fluid that is flowing in a first direction comprising:
   an irradiating optical system for producing scattered light by irradiating the minute particles from a second direction that is substantially perpendicular to the first direction including:
   an irradiating means for providing a laser beam;
   a first lens means for flattening the laser beam so that it is short in the first direction and long in the second direction;
   a photointensity-compensating means for converting the distribution of integrated photointensity values of the flattened laser beam into a square pattern, the minute particles being irradiated by the flattened and compensated laser beam, and
   a detecting optical system having an axis that is substantially perpendicular to the first and the second directions including:
   a second lens means for focusing the scattered light from a section of the fluid and for forming a real image thereof, and
   a slit member detecting means having a detecting slit thereon, the perimeter of the detecting slit cutting the real image of the scattered light in the second direction but not in the first direction so as to reduce the influence of aberration and dislocation of focus in the detecting optical system.

2. The particle counter of claim 1 wherein the photointensity compensating means comprises a planar member having a slit thereon.

3. The particle counter of claim 1 wherein the photointensity compensating means comprises a space filter and a soft aperture.

4. A method of measuring the concentration and particle-size distribution of minute particles contained in a fluid that is flowing in a first direction comprising the steps of;
   providing a laser beam from a second direction that is substantially perpendicular to the first direction;
   flattening the laser beam with a lens system so that it is short in the first direction and long in the second direction;
   converting the distribution of the integrated photointensity values of the flattened laser beam into a square pattern;
   irradiating the minute particles in a central portion of the fluid whereby the light of the laser beam is scattered by the particles;
   focusing the scattered light in a third direction that is substantially perpendicular to the first and the second directions so as to form a real image thereof in the third direction;
   limiting the incidence of the real image in the second direction but not in the first direction, and
   detecting the limited real image.

5. The method of claim 4 wherein the converting step comprises the step of shining the flattened laser beam through a member having a slit thereon.

6. A particle counter comprising:
   an irradiating optical system for irradiating a central portion in a fluid to be measured flowing at an appointed velocity of flow, where a velocity of flow distribution is uniform as far as possible, with laser beams from a side in a direction meeting at right angles with a flow direction of said fluid to be measured,
   a detecting optical system for detecting scattered lights of said laser beams by minute particles contained in said fluid to be measured;
   said irradiating optical system being provided with a photointensity-compensating means for turning a distribution of integrated values of the photointensity in a direction meeting at right angles with said flow direction of the fluid to be measured and an irradiating direction of the laser beams (values integrated in the flow direction of the fluid to be measured) into a square shape, and
   said detecting optical system being provided with a slit member provided with a slit having a width with sufficient room in a direction meeting at right angles with the irradiating direction of said laser beams at an image-forming position thereof.

* * * * *